United States Patent
Temporin et al.

(10) Patent No.: US 9,117,618 B2
(45) Date of Patent: Aug. 25, 2015

(54) ION GENERATING APPARATUS

(71) Applicant: Sharp Kabushiki Kaisha, Osaka-shi, Osaka (JP)

(72) Inventors: Noriko Temporin, Osaka (JP); Shohgo Yukawa, Osaka (JP); Makoto Kitahira, Osaka (JP); Shigeyuki Harada, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 0 days.

(21) Appl. No.: 14/386,040

(22) PCT Filed: Mar. 21, 2013

(86) PCT No.: PCT/JP2013/058101
§ 371 (c)(1),
(2) Date: Sep. 18, 2014

(87) PCT Pub. No.: WO2013/150899
PCT Pub. Date: Oct. 10, 2013

(65) Prior Publication Data
US 2015/0083931 A1    Mar. 26, 2015

(30) Foreign Application Priority Data
Apr. 5, 2012 (JP) ................... 2012-086070

(51) Int. Cl.
*H01J 27/08* (2006.01)
*A61L 9/00* (2006.01)
(Continued)

(52) U.S. Cl.
CPC . *H01J 27/08* (2013.01); *A61L 9/22* (2013.01); *H01T 23/00* (2013.01)

(58) Field of Classification Search
CPC ....... H01J 37/3171; H01J 37/16; H01J 37/04; H01J 37/08; H01J 27/02; H01J 27/04; H01J 27/08; H01J 27/14; H01J 27/022; H01J 49/0422; H01J 49/168; H01T 23/00; H01T 19/04; H05H 3/06; H05H 15/00; H05H 6/00; H01L 27/10805; H01L 27/10873; H01L 27/11
USPC ........... 250/423 R, 288, 492.1; 376/114, 116, 376/121, 157
See application file for complete search history.

(56) References Cited

U.S. PATENT DOCUMENTS

2004/0036020 A1* 2/2004 Sakairi et al. ................. 250/288
2007/0235663 A1* 10/2007 Low et al. ................. 250/492.1
(Continued)

FOREIGN PATENT DOCUMENTS

JP    2004-319358 A    11/2004
JP    2008-108521 A    5/2008
(Continued)

OTHER PUBLICATIONS

Official Communication issued in International Patent Application No. PCT/JP2013/058101, mailed on May 21, 2013.

*Primary Examiner* — David A Vanore
(74) *Attorney, Agent, or Firm* — Keating & Bennett, LLP

(57) ABSTRACT

A discharge electrode 5 for generating ions and a high-voltage generating circuit unit 2 that supplies the discharge electrode 5 with a high voltage are housed in a housing 3. A discharge opening 12 for discharging the generated ions is formed in the housing 3. The housing 3 is covered by an exterior case 15. The exterior case 15 is connected to the high-voltage generating circuit unit 2 and functions as an induction electrode. A passage opening 33 leading to the discharge opening 12 is formed in the exterior case 15. An insulating sheet 36 covers the periphery of the passage opening 33 in the exterior case 15 facing a space into which the ions are discharged so that the discharged ions do not attach to the exterior case 15. Decrease in the amount of discharged ions can be prevented while using a peripheral component of the discharge electrode 5 as the induction electrode.

7 Claims, 5 Drawing Sheets

(51) Int. Cl.
*A61L 9/22* (2006.01)
*H01T 23/00* (2006.01)

(56) References Cited

U.S. PATENT DOCUMENTS

2007/0237281 A1* 10/2007 Yakovlyev .................... 376/157
2008/0067410 A1* 3/2008 Shigehiro et al. ......... 250/423 R
2008/0067411 A1* 3/2008 Nishino et al. ............ 250/423 R
2008/0277593 A1* 11/2008 Fujita et al. ............... 250/423 R
2011/0044418 A1* 2/2011 Stubbers et al. .............. 376/116

FOREIGN PATENT DOCUMENTS

| JP | 2008-123917 A | 5/2008 |
| JP | 2009-266664 A | 11/2009 |
| JP | 2011-96555 A | 5/2011 |
| WO | 2008/108331 A1 | 9/2008 |

* cited by examiner

ION GENERATING APPARATUS

TECHNICAL FIELD

The present invention relates to an ion generating apparatus that generates ions in the air by corona discharge.

BACKGROUND ART

An ion generating apparatus that generates ions by corona discharge has a discharge electrode and an induction electrode. To perform stable corona discharge, the distance between the discharge electrode and the induction electrode is required to be maintained with high accuracy. This issue can be resolved if the induction electrode is eliminated. In PTL 1, an ion generating apparatus that uses a constituent component provided near the discharge electrode as the induction electrode is described. In this ion generating apparatus, a support body that is a circuit board that supports the discharge electrode is connected to a high-voltage generating circuit, and the support body functions as the induction electrode.

CITATION LIST

Patent Literature

PTL 1: Japanese Unexamined Patent Application Publication No. 2011-96555

SUMMARY OF INVENTION

Technical Problem

In the above-described ion generating apparatus, a high voltage is applied between the discharge electrode and the support body. Therefore, electromagnetic noise may be generated and adversely affect peripheral electrical equipment. To reduce the effects of the electromagnetic noise, the discharge electrode and the support body are housed within a metal exterior case. However, the generated ions attach to the metal exterior case, and the discharged ions decrease.

In light of the above-described issues, an object of the present invention is to provide an ion generating apparatus that is capable of preventing decrease in the amount of discharged ions while using a peripheral component of a discharge electrode as an induction electrode.

Solution to Problem

In the present invention, a discharge electrode for generating ions and a high-voltage generating circuit unit that supplies the discharge electrode with a high voltage are housed in a housing. A discharge opening for discharging the generated ions is formed in the housing. The housing is covered by a shield case. The shield case is connected to the high-voltage generating circuit unit and functions as an induction electrode. The outer surface of the shield case facing a space into which the ions are discharged is covered by an insulating section so that the discharged ions do not attach to the shield case.

As a result of the shield case that is present in the periphery of the discharge electrode serving as the induction electrode, a separate induction electrode is no longer required to be provided. When a high voltage is applied between the discharge electrode and the shield case, ions are generated and discharged from the discharge opening in the housing from the discharge opening. The shield case that covers the housing is covered by the insulating section. Therefore, the ions do not attach to the shield case.

A passage opening leading to the discharge opening is formed in the shield case. A rib that projects outward is formed on a peripheral edge of the discharge opening in the housing. The rib covers an inner peripheral surface of the passage opening in the shield case. Therefore, the rib functions as the insulating section that covers the inner peripheral surface of the passage opening in the shield case. As a result, ions that are passing through do not attach to the inner peripheral surface of the shield case.

The insulating section covers the periphery of the passage opening in the shield case. The periphery of the passage opening in the shield case faces the space into which the ions are discharged. However, as a result of the periphery being covered by the insulating section, the shield case is not exposed to the space into which the ions are discharged, and attachment of the ions to the shield case can be prevented.

The high-voltage generating circuit unit has a high-voltage transformer. The shield case is connected to a secondary side of the high-voltage transformer. The shield case is ground-connected by a capacitor. The capacitor is interposed between a primary side and the secondary side of the high-voltage transformer. The shield case that is connected to the ground as a measure against noise can be used as the induction electrode. In addition, unnecessary current flowing between the primary side and the secondary side can be cut by the capacitor. Noise reduction effect can be improved.

The discharge electrode is connected to the high-voltage generating circuit unit by a noise reducing element. Noise current flowing to the discharge electrode can be reduced, and generation of electromagnetic noise can be suppressed.

Advantageous Effects of Invention

According to the present invention, as a result of the shield case being used as an induction electrode, a component to be used as an induction electrode can be eliminated, and size reduction of the apparatus can be achieved. In addition, because the outer surface of the shield case is covered by the insulating section, loss of generated ions due to attachment to the shield case can be prevented.

DESCRIPTION OF EMBODIMENTS

Figure 1:
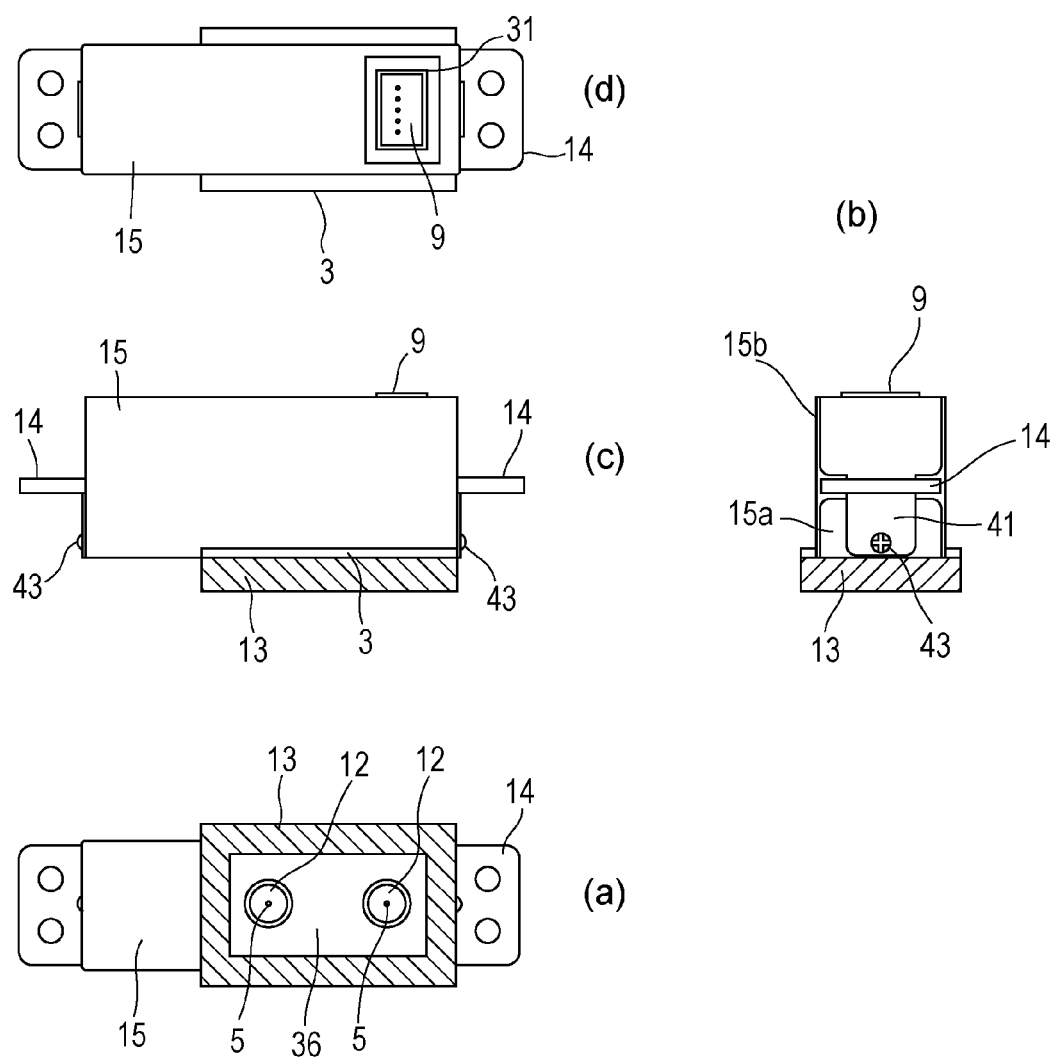
FIG. 1 shows an outer appearance of an ion generating apparatus of the present invention, in which (a) is a front view, (b) is a side view, (c) is a planar view, and (d) is a rear view.
Figure 2:
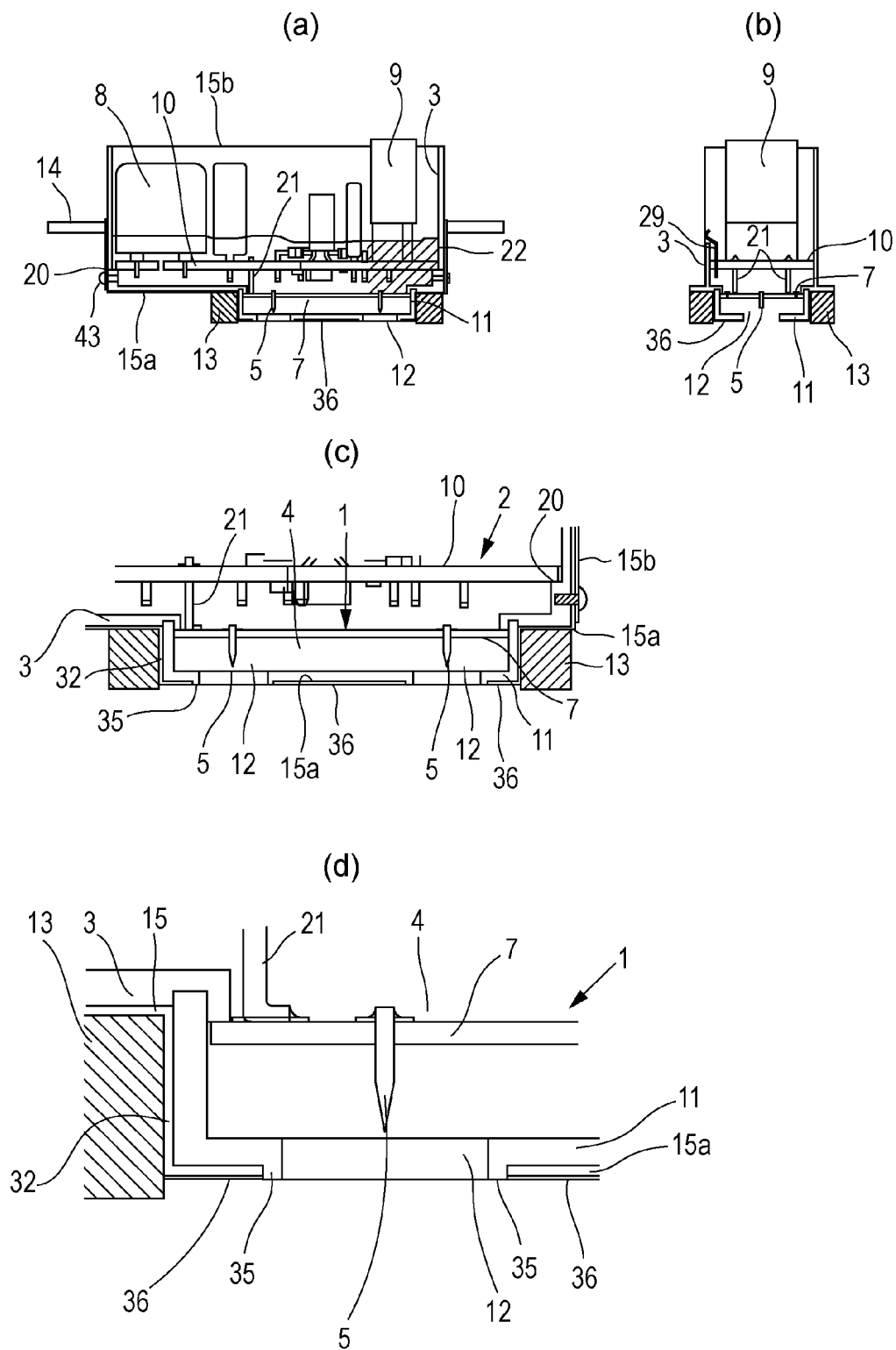
FIG. 2 shows an internal structure of the ion generating apparatus, in which (a) is a cross-sectional view viewed from above, (b) is a cross-sectional view viewed from the side, (c) is a cross-sectional view near discharge openings of a housing, and (d) is an enlarged cross-sectional view of the discharge opening.
Figure 3:
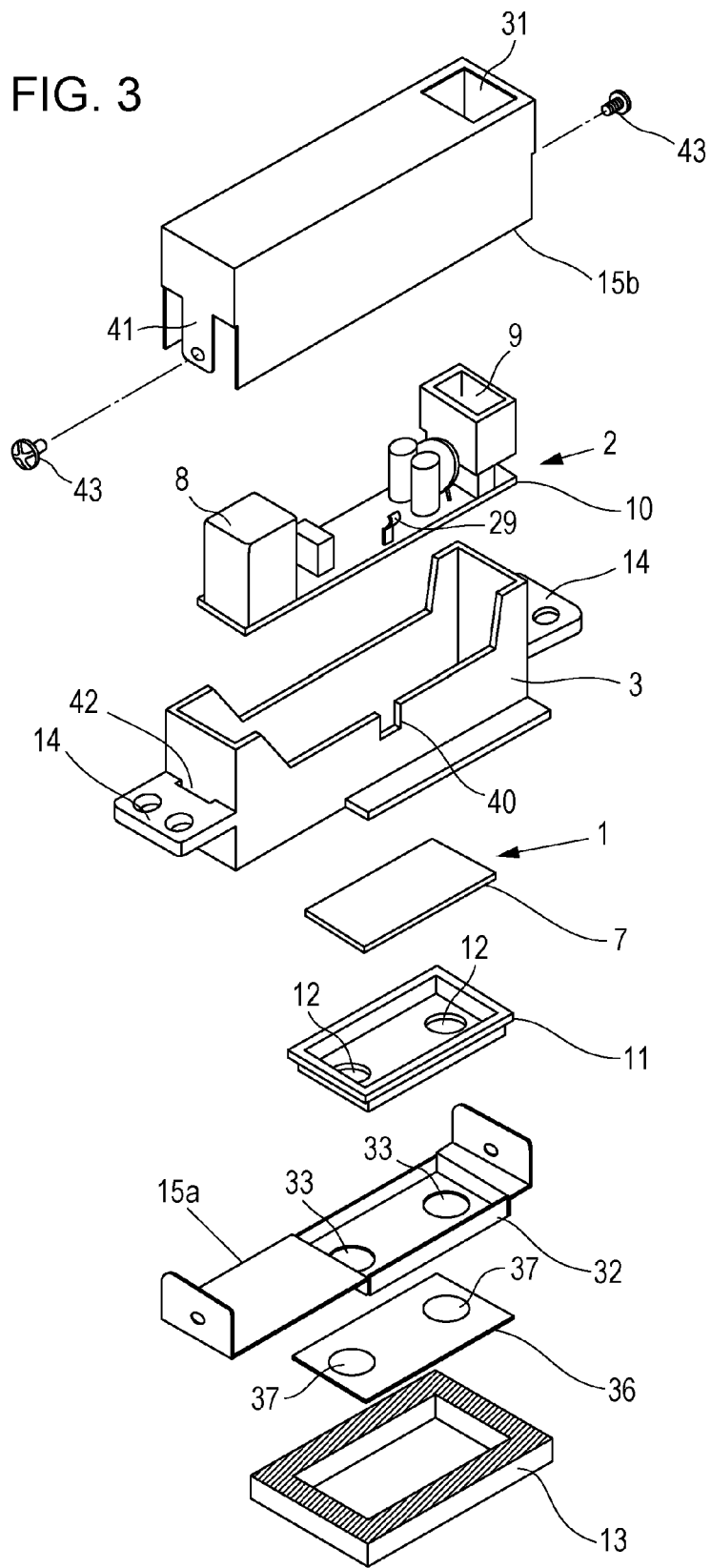
FIG. 3 is an exploded perspective view of the ion generating apparatus.

An ion generating apparatus according to a present embodiment is shown in FIG. 1 to FIG. 3. The ion generating apparatus includes an ion generating element 1 that generates ions, a high-voltage generating circuit unit 2 that supplies a high voltage to the ion generating element 1, and a housing 3 that houses the ion generating element 1 and the high-voltage generating circuit unit 2. The housing 3 is formed into a box shape using a resin. An opening 4 for ion generating element attachment is formed on the front surface of the housing 3. The back surface of the housing 3 is open. The ion generating element 1 is mounted to the housing 3 at the opening 4. The high-voltage generating circuit unit 2 is mounted within the housing 3.

The ion generating element 1 has discharge electrodes 5. The discharge electrode 5 is a needle-shaped electrode. Positive and negative discharge electrodes 5 are both mounted on a circuit board 7. The circuit board 7 is fitted into the opening 4 of the housing 3. The outer peripheral portion of the circuit board 7 is bonded to the housing 3, and the circuit board 7 is thereby attached. A discharge cover 11 in which discharge openings 12 for ions are formed is attached by bonding to the housing 3 so as to cover the ion generating element 1. The resin discharge cover 11 is integrated with the housing 3. In other words, the discharge cover 11 becomes part of the housing 3, and the circular discharge openings 12 are formed in the housing 3. The periphery of the discharge cover 11 is surrounded by a sealing member 13. When the ion generating apparatus is attached to a duct, the sealing member 13 comes into close contact with the wall surface of the duct and seals air leakage. Reference numeral 14 in the drawings represents a fixing leg for attachment.

The housing 3 is covered by an exterior case 15 which is a shield case having electrical conductivity, to reduce electromagnetic noise that leaks from the apparatus. The metal exterior case 15 covers the outer surface of the housing 3, excluding the discharge openings 12.

The high-voltage generating circuit unit 2 has a high-voltage transformer 8, a connector 9, and a control board 10 on which electronic components and the like are mounted. The control board 10 is housed in the housing 3 and supported by a board supporting section 20 that is provided on the inner wall of the housing 3.

The control board 10 of the high-voltage generating circuit unit 2 and the circuit board 7 of the ion generating element 1 are electrically connected by a plurality of connection terminals 21. The high-voltage transformer 8 and the positive and negative discharge electrodes 5 are electrically connected by the connection terminals 21. The high-voltage transformer 8 is covered by an electrically conductive shield cap.

The control board 10 of the high-voltage generating circuit unit 2 is sealed within the housing 3 by a filler resin 22, excluding the print pattern, the conduction terminals of the electronic components, and the connection conduction terminals of the connector 9. As a result of this molding, anti-moisture insulation of the high-voltage generating circuit unit 2 is ensured. When the housing 3 is filled with the filler resin 22, the circuit board 7 of the ion generating element 1 seals the opening 4 of the housing 3 so that the filler resin 22 does not leak.

Figure 4:
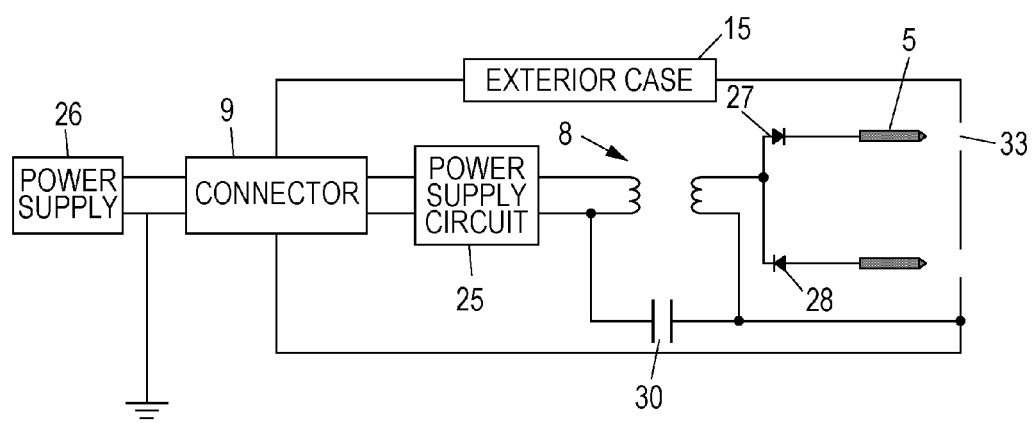
FIG. 4 is a schematic diagram of an electrical circuit in the ion generating apparatus.

As shown in FIG. 4, the high-voltage generating circuit unit 2 includes a power supply circuit 25 that drives the high-voltage transformer 8. The power supply circuit 25 that is mounted on the control board 10 is connected to the connector 9 for power supply input. Power is supplied to the power supply circuit 25 from the connector 9 that is connected to an external power supply 26, such as a commercial power supply.

The power supply circuit 25 that has been supplied power operates and outputs an oscillation signal for high-voltage generation. The high-voltage transformer 8 which has received the oscillation signal from the power supply circuit 25 and is being driven generates a high voltage and outputs the high voltage to the positive discharge electrode 5 and the negative discharge electrode 5.

The positive discharge electrode 5 and the negative discharge electrode 5 are connected by diodes 27 and 28 to one output terminal of a secondary-side coil of the high-voltage transformer 8. The diode 27 that is connected to the positive discharge electrode 5 is disposed in a direction opposite to that of the diode 28 connected to the negative discharge electrode 5.

As shown in FIG. 2, the exterior case 15 is in contact with a contact terminal 29 that is attached to the control board 10. The external case 15 is connected to the high-voltage generating circuit unit 2 by the contact terminal 29 and functions as an induction electrode. As shown in FIG. 4, the exterior case 15 is connected to the other output terminal of the secondary-side coil of the high-voltage transformer 8. A high voltage is applied between the discharge electrodes 5 and the exterior case 15.

In addition, the exterior case 15 is ground-connected by the high-voltage generating circuit unit 2, and is thereby grounded. The exterior case 15 is connected to an intermediate point between a primary-side coil of the high-voltage transformer 8 and the power supply circuit 25 by a capacitor 30. As a result, the primary side and the secondary side of the high-voltage transformer 8 are connected by the capacitor 30.

The exterior case 15 is divided into a front case 15a and a back case 15b that are composed of metal. The back case 15b is formed into a box shape of which the front surface is open and houses the housing 3. A connector opening 31 is formed on the back surface of the back case 15b. The front case 15a is formed into a lid shape and covers the front surface of the housing 3 on which the discharge cover 11 is attached. A portion of the front case 15a that covers the discharge cover 11 projects towards the front, thereby forming a projecting section 32. A pair of circular passage openings 33 that lead to each discharge opening 12 are formed in the projecting section 32.

A ring-shaped rib 35 is formed on the peripheral edges of the discharge openings 12 in the housing 3. The rib 35 is formed so as to project towards the front (outer side), and projects further towards the front than the projecting section 32 of the exterior case 15. The passage opening 33 in the exterior case 15 has a larger diameter than the discharge opening 12. The rib 35 is fitted into the passage opening 33, and the inner peripheral surface of the passage opening 33 is in close contact with the rib 35. In other words, the inner peripheral surface of the passage opening 33 is covered by the rib 35.

The sealing member 13 is provided in the periphery of the projecting section 32 of the exterior case 15. The sealing member 13 is formed into a frame shape by an elastic material, such as rubber, so as to surround the projecting section 32. When the sealing member 13 is attached to the exterior case 15 and the ion generating apparatus is attached to a duct or the like, the sealing member 13 seals the space between the duct and the exterior case 15 and prevents air leakage.

Here, the exterior case 15 is covered by an insulating section so that discharged ions do not attach thereto. The projecting section 32 of the exterior case 15 is covered by an electrically insulating covering sheet 36. The covering sheet 36 serves as the insulating section. Two holes 37 that correspond to the passage openings 33 are formed in the resin covering sheet 36. The covering sheet 36 is attached to the front surface of the projecting section 32 so as to cover the periphery of the passage openings 33. The thickness of the covering sheet 36 is set so that the rib 35 is flush with the covering sheet 36 or projects further towards the front than the covering sheet 36.

In addition, the inner peripheral surface of the passage opening 33 in the exterior case 15 is covered by the electrically insulating rib 35 of the housing 3. The rib 35 also functions as the insulating section.

Next, an assembly procedure of the ion generating apparatus will be described with reference to FIG. 3. First, the circuit board 7 of the ion generating element 1 is attached by bonding to the opening 4 of the housing 3. The discharge cover 11 is attached by bonding to the front surface of the housing 3 so as to cover the opening 4 of the housing 3. Next, with the back surface of the housing 3 facing upwards, the control board 10 is inserted into the housing 3. The control board 10 is supported by the board supporting section 20. At this time, the tip of the contact terminal 29 is in a state protruding outside from a notch 40 formed in the housing 3. In addition, the connection terminals 21 attached to the circuit board 7 of the ion generating element 1 are fitted into throughholes in the control board 10 and soldered to the control board 10.

Then, the filler resin 22 is injected into the housing 3 from above. After the filler resin 22 is cured, the front case 15a covers the front surface of the housing 3, and the back case 15b covers the back surface of the housing 3. A fixing piece 41 is formed on the side surface of the back case 30b. The fixing piece 41 is inserted into a through hole 42 formed in the fixing leg 14 of the housing 3. The fixing piece 41 overlaps with the side surface of the front case 15a and is fixed by a screw 43. As a result, the front case 15a and the back case 15b are joined, thereby forming a single exterior case 15. The contact terminal 29 comes into contact with the inner surface of the exterior case 15, and the exterior case 15 is connected to the ground. As a result, the effect of electromagnetic noise reduction by the exterior case 15 can be achieved.

The covering sheet 36 is attached to the front surface of the projecting section 32 in the front case 15a of the exterior case 15. The sealing member 13 is attached to the front case 15a in the periphery of the projecting section 32.

Figure 5:
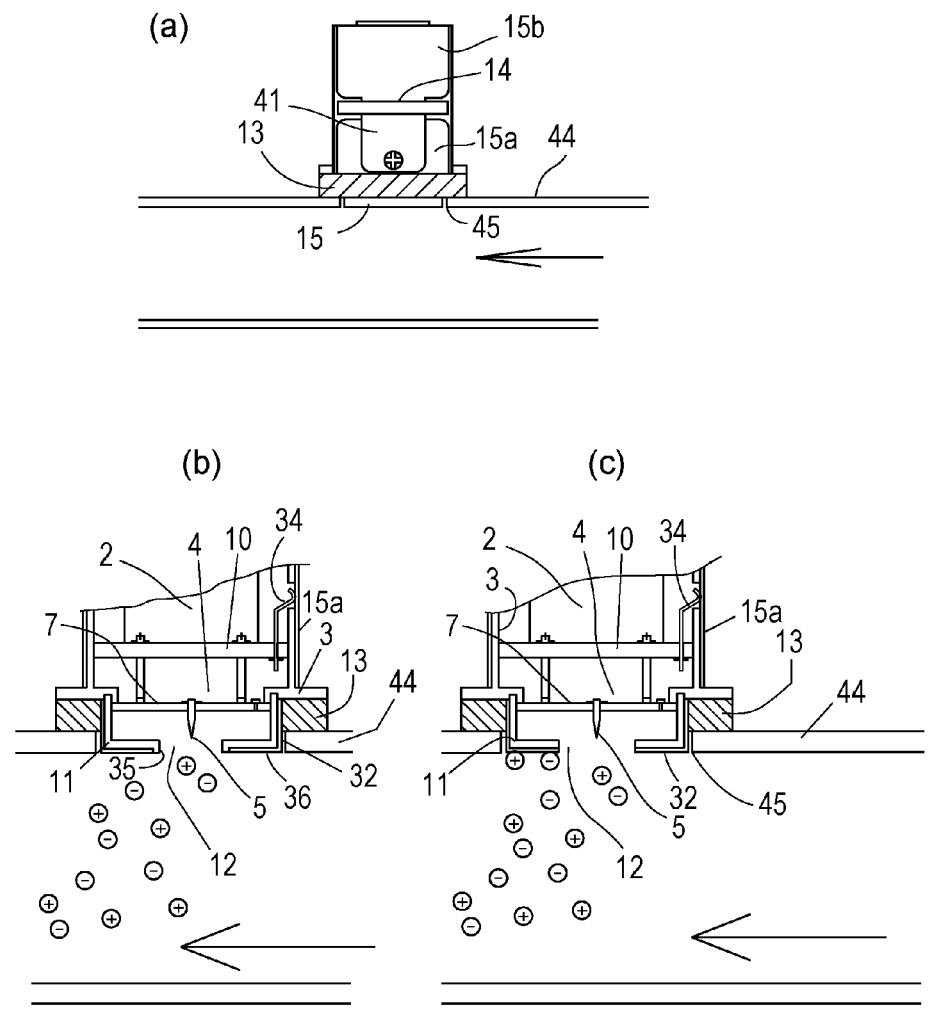
FIG. 5 shows the ion generating apparatus attached to a duct, in which (a) is an attachment diagram, (b) is a diagram showing the movement of ions when an insulating section is provided, and (c) is a diagram showing the movement of ions when an insulating section is not provided.

The ion generating apparatus that has been assembled as described above is incorporated into electrical equipment, such as an air conditioner. The electrical equipment is provided with an air blowing path for discharging the generated ions into a room by blowing air. As shown in FIG. 5, the ion generating apparatus is attached to a duct 44 that forms the air blowing path.

An attachment opening 45 is formed in the peripheral wall of the duct 44. The discharge cover 11 of the housing 3 is fitted into the attachment opening 45. The sealing member 13 comes into close contact with the outer wall of the duct 44, thereby sealing the space between the housing 3 and the duct 44. Air leakage from the duct 44 to outside of the duct 44 is prevented.

The front surface of the discharge cover 11 of the housing 3 faces the interior of the duct 44, and the discharge openings 12 communicate with the duct 44. At this time, the covering sheet 36 is exposed within the duct 44, and the exterior case 15 is hidden so as to not face the duct 44. The front surface of the discharge cover 11 projects slightly further into the duct 44 than the peripheral wall of the duct 44. Therefore, the front surface of the projecting section 32 covered by the covering sheet 36 is positioned within the duct 44.

When the ion generating apparatus is driven, the high-voltage generating circuit unit 2 operates. A high voltage is applied between the discharge electrodes 5 and the exterior case 15 that serves as the induction electrode, by operation of the high-voltage transformer 8. Corona discharge occurs at the tip of each discharge electrode 5. Positive ions and negative ions are generated at the tips of the discharge electrodes 5. At the positive discharge electrode 5, negative ions flow through the diode 27 and only positive ions are discharged. At the negative discharge electrode 5, positive ions flow through the diode 28, and only negative ions are discharged.

As a result of the exterior case 15 which is provided to reduce generated electromagnetic noise being used as the induction electrode, a separate electrode is no longer required to be provided. As a result, components are reduced, assembly steps are reduced, and cost can be reduced. Furthermore, because a separate induction electrode is eliminated, the area near the discharge openings of the housing 3 can be made compact, and size reduction of the ion generating apparatus can be achieved.

In addition, even when electrically conductive foreign matter infiltrates the interior of the housing 3 from the discharge opening 12, only insulating materials are near the discharge electrodes 5. Therefore, short circuit of the discharge electrodes 5 does not occur, and malfunction of the ion generating apparatus can be prevented. Furthermore, short circuits can be similarly prevented even when water infiltration and condensation occur.

As a result of the primary side and the secondary side of the high-voltage transformer 8 being connected by the capacitor 30, only the alternating current accompanying discharge can be directly connected. During an abnormality, the direct current component of the high-frequency current flowing to the primary side can be cut. During an abnormality, the direct current component can be prevented from flowing to the secondary side, thereby improving safety. In addition, the alternating current component can be sent to the ground (GND) rather than being sent to the secondary side. Generation of radiation noise can be reduced.

Figure 6:
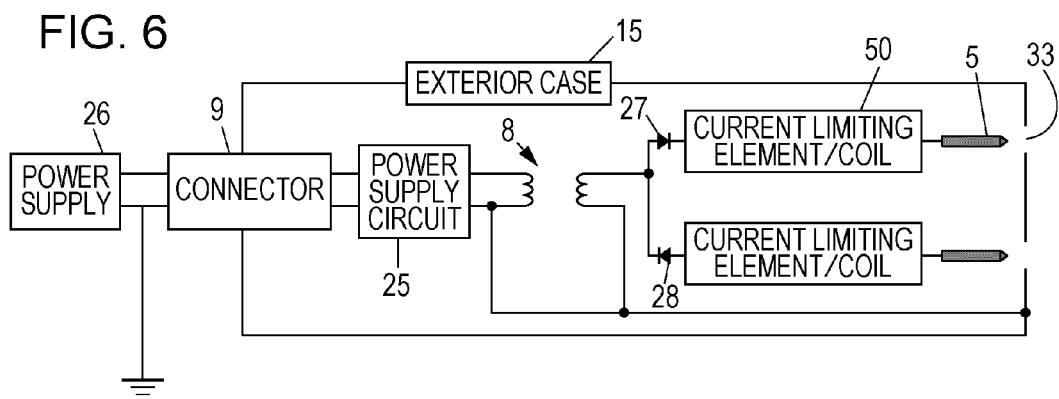
FIG. 6 is a schematic diagram of an electrical circuit in an ion generating device according to another embodiment.

To reduce the generation of electromagnetic noise, as shown in FIG. 6, the discharge electrodes 5 are connected to the high-voltage generating circuit unit 2 by noise reducing elements 50. The noise reducing elements 50 are current limiting elements or coils, and are interposed between the discharge electrodes 5 and the respective diodes 27 and 28. The current limiting element is a resistor or the like. By the noise reducing element 50, noise current flowing to the discharge electrode 5 can be reduced, and the generation of electromagnetic noise can be reduced. In the drawing, the capacitor 30 is not interposed between the primary side and the secondary side of the high-voltage transformer 8. However, the capacitor 30 may be disposed therebetween.

The ions generated by the above-described discharge electrodes 5 are discharged from the discharge openings 12 into the duct 44. The ions are then carried by the blowing air within the duct 44, and wind including a high concentration of ions is blown out from the outlet of the duct 44.

The positive ion generated here is a cluster ion in which a plurality of water molecules are attached around a hydrogen ion ($H^+$). The positive ion is expressed by $H^+(H_2O)_m$ (m represents zero or an arbitrary natural number). In addition, the negative ion is a cluster ion in which a plurality of water molecules are attached around an oxygen ion ($O_2^-$). The negative ion is expressed by $O_2^-(H_2O)_n$ (n represents zero or an arbitrary natural number).

When ions of both polarities, the positive ions and the negative ions, are discharged, substantially equal amounts of $H^+(H_2O)_m$ (m represents zero or an arbitrary natural number) that are the positive ions in the air and $O_2^-(H_2O)_n$ (n represents zero or an arbitrary natural number) that are the negative ions are generated. Both ions surround fungi and viruses floating in the air and attach to the fungi and viruses. As a result of the workings of hydroxyl radicals (.OH) that are active species generated at this time, the floating fungi and the like can be removed.

As shown in FIG. 5(b), the covering sheet 36 is provided on the projecting section 32 of the exterior case 15 facing the duct 44. Therefore, the front surface of the exterior case 15 that comes into contact with the ions is electrically insulated. Therefore, the ions that are discharged from the discharge openings 12 do not attach to the exterior case 15. As shown in FIG. 5(c), when the covering sheet 36 is not present, the front surface of the exterior case 15 is exposed to the outside. Some of the discharged ions are attracted to the electric load of the exterior case 15 and attach to the front surface of the exterior case 15. Therefore, the amount of ions discharged from the duct 44 decreases. Through experiments, a result indicating that about ten percent of the ions attach to the exterior case 15 has been obtained. However, as a result of the covering sheet 36 being provided, the ions no longer attach to the exterior case 15, and decrease in the amount of discharged ions can be prevented. The amount of ions discharged from the duct 44 can be sufficiently ensured.

In this way, it is important that the covering sheet 36 be provided so that the outer surface of the exterior case 15 that may come into contact with the ions is not exposed. Therefore, the covering sheet 36 may be adhered so as to also cover the end surfaces of the passage openings 33 of the exterior case 15. In addition, the covering sheet 36 is not required to be provided on the overall surface of the exterior case 15. In other words, the covering sheet 36 may be provided on only the outer surface of the exterior case 15 to which the ions discharged from the discharge openings 12 of the housing 3 may attach. For example, when the front surface of the projecting section 32 faces the duct 44, the covering sheet 36 is provided on the front surface of the projecting section 32. However, when the overall housing 3 is disposed within the duct 44, the overall surface of the shield case 33 is required to be covered by the covering sheet 36.

As described above, the housing 3 can be covered by the exterior case 15 excluding sections which cannot be covered in terms of function. Therefore, electromagnetic noise can be more easily suppressed compared to when electromagnetic noise reduction measures are taken regarding the control board or the electronic components. Consequently, application to apparatuses that involve discharge and compact ion generating apparatuses that have a high-voltage generating circuit unit becomes possible. In addition, electromagnetic noise can be reduced even when such ion generating apparatuses are mounted in various products including electrical equipment, such as air-conditioners, air purifiers, refrigerators, and vacuum cleaners, and vehicles such as automobiles.

The present invention is not limited to the above-described embodiment. Numerous alterations and modifications can obviously be made to the above-described embodiment within the scope of the present invention. An insulating film may be formed by coating as the insulating section. The insulating film is formed by an electrically insulating material being coated or sprayed onto the surface of a shield case that may come into contact with the ions.

In addition, the rib may not be provided in the housing. In this instance, the end surfaces of the passage openings in the shield case are exposed. Therefore, the insulating section, such as the covering sheet, is also provided on the end surfaces of the passage openings.

REFERENCE SIGNS LIST 1 ion generating element
2 high-voltage generating circuit unit
3 housing
4 opening
5 discharge electrode
8 high-voltage transformer
11 discharge cover
12 discharge opening
15 exterior case
25 power supply circuit
27 diode
28 diode
30 capacitor
32 projecting section
33 passage opening
35 rib
36 covering sheet
50 noise reducing element

The invention claimed is:

1. An ion generating apparatus, comprising:
   a discharge electrode configured to generate ions; and
   a voltage generating circuit configured to supply the discharge electrode with a voltage;
   a housing configured to house the discharge electrode and the high-voltage generating circuit, the housing including a discharge opening configured to discharge the generated ions; and
   a shield case configured to cover the housing, wherein
   the shield case is connected to the voltage generating circuit and configured to function as an induction electrode, and
   the shield case includes an outer surface facing a space into which the ions are discharged, the outer surface of the shield case being covered by an insulating section so that the discharged ions do not attach to the shield case.

2. The ion generating apparatus according to claim 1, further comprising:
   voltage transformer included in the voltage generating circuit,
   wherein the shield case is connected to a secondary side of the voltage transformer.

3. The ion generating apparatus according to claim 1, further comprising:
   a capacitor configured to ground the shield case.

4. The ion generating apparatus according to claim 3,
   wherein the capacitor is interposed between a primary side and the secondary side of the voltage transformer.

5. The ion generating apparatus according to claim 1, further comprising:
   a noise reducing circuit configured to connect the discharge electrode and the voltage generating circuit.

6. The ion generating apparatus according to claim 1, further comprising:
   a passage opening leading to the discharge opening formed in the shield case; and
   a rib that projects outward formed on a peripheral edge of the discharge opening in the housing;
   wherein the rib covers an inner peripheral surface of the passage opening in the shield case.

7. The ion generating apparatus according to claim 6,
   wherein the insulating section covers the periphery of the passage opening in the shield case.

* * * * *